US00PP28303P2

(12) United States Plant Patent
Ichiba

(10) Patent No.: US PP28,303 P2
(45) Date of Patent: Aug. 15, 2017

(54) ***SCABIOSA* PLANT NAMED 'ICHPIN'**

(50) Latin Name: ***Scabiosa* hybrid**
Varietal Denomination: ICHPIN

(71) Applicant: Kaori Ichiba, Tokyo (JP)

(72) Inventor: Kaori Ichiba, Tokyo (JP)

( * ) Notice: Subject to any disclaimer, the term of this patent is extended or adjusted under 35 U.S.C. 154(b) by 41 days.

(21) Appl. No.: 14/757,297

(22) Filed: Dec. 14, 2015

(51) Int. Cl.
*A01H 5/02* (2006.01)

(52) U.S. Cl.
USPC ..... Plt./478

(58) Field of Classification Search
USPC ..... Plt./478
See application file for complete search history.

*Primary Examiner* — Keith Robinson
(74) *Attorney, Agent, or Firm* — Penny J. Aguirre

(57) ABSTRACT

A new cultivar of *Scabiosa*, 'ICHPIN', that is characterized by its very long blooming period, May through November in the United Kingdom and Netherlands and has shown continuous bloom 12 months and longer in Mediterranean climates of California, its plant height that reaches 90 cm in height in bloom (foliage height of 50 cm), its and its inflorescences that are held on long peduncles and very bright pink in color with white coloration in centers as temperatures cool later in the season.

2 Drawing Sheets

Botanical classification: *Scabiosa* hybrid.
Variety denomination: 'ICHPIN'.

BACKGROUND OF THE INVENTION

The present invention relates to a new and distinct cultivar of *Scabiosa* of hybrid origin, botanically known as *Scabiosa* 'ICHPIN' and will be referred to hereinafter by its cultivar name, 'ICHPIN'.

The new invention arose from an ongoing controlled breeding program conducted by the Inventor in Tokyo Japan working with collections of the species *Scabiosa columbaria* and *Scabiosa japonica*, and many hybrids of different species of *Scabiosa*. An objective of this program was to obtain new cultivars of *Scabiosa* that are healthy with good vigor, very long blooming, have desirable plant heights combined with unique flower colors.

The new cultivar arose from crosses made over a number of years between unnamed and unpatented plants from the Inventor's breeding program and seeds were pooled from the crosses and sown. The exact parentage is unknown. The new cultivar was selected in 2008 as a single unique plant from the above crosses.

Asexual propagation of the new cultivar was first accomplished by the Inventor by stem cuttings in 2008 in Tokyo, Japan. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of 'ICHPIN'. These characteristics in combination distinguish 'ICHPIN' as a new and distinct cultivar of *Scabiosa*.

1. 'ICHPIN' exhibits a very long blooming period, blooming from May through November in the United Kingdom and Netherlands and has shown continuous bloom 12 months and longer in Mediterranean climates of California.
2. 'ICHPIN' exhibits a plant height that reaches 90 cm in height in bloom (foliage height of 50 cm).
3. 'ICHPIN' exhibits inflorescences held on long peduncles.
4. 'ICHPIN' exhibits inflorescences that are very bright pink in color with white coloration in centers as temperatures cool later in the season.

'ICHPIN' can be most closely compared to the *Scabiosa columbaria* cultivars, 'Pink Mist' (U.S. Plant Pat. No. 8,957) and 'Butterfly Blue' (not patented). 'Pink Mist' differs from 'ICHPIN' in having a much shorter plant habit, shorter peduncles, and having inflorescences that are light pink in color. 'Butterfly Blue' differs from 'ICHPIN' in in having a much shorter plant habit, shorter peduncles, and having inflorescences that are lilac blue in color.

BRIEF DESCRIPTION OF THE DRAWINGS

The accompanying colored photographs illustrates the overall appearance and distinct characteristics of plants of the new *Scabiosa*.

The photograph in FIG. 1 provides a side view of 'ICHPIN' 18 months in age as grown in a 5-liter container in a glass greenhouse in Watsonsville, Calif.

Figure 1:
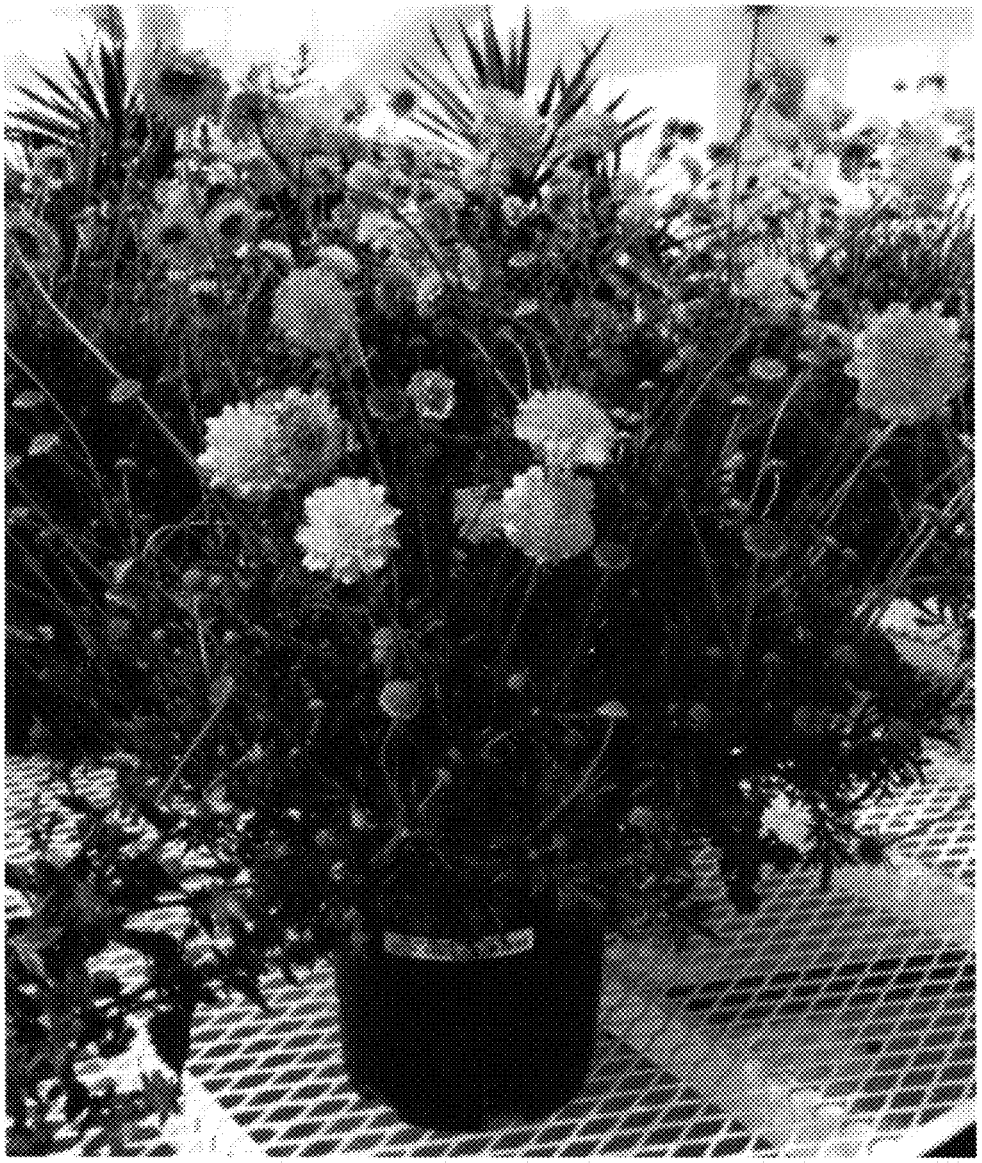
Figure 2:
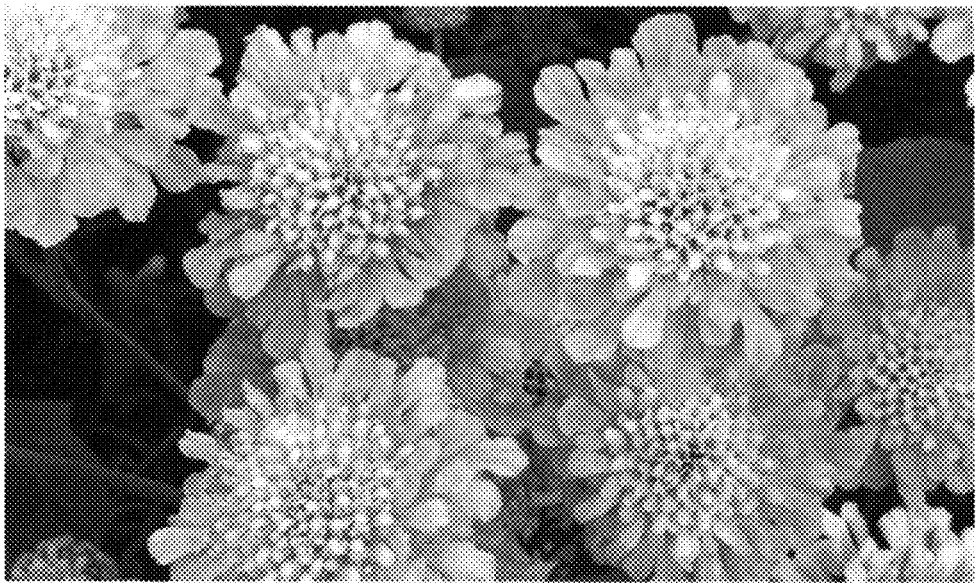

The photograph in FIG. 2 provides a close-up view of the inflorescences of 'ICHPIN' on a plant 18 months in age as grown outdoors in a 5-liter container in Maldon, Essex, United Kingdom.

Figure 3:
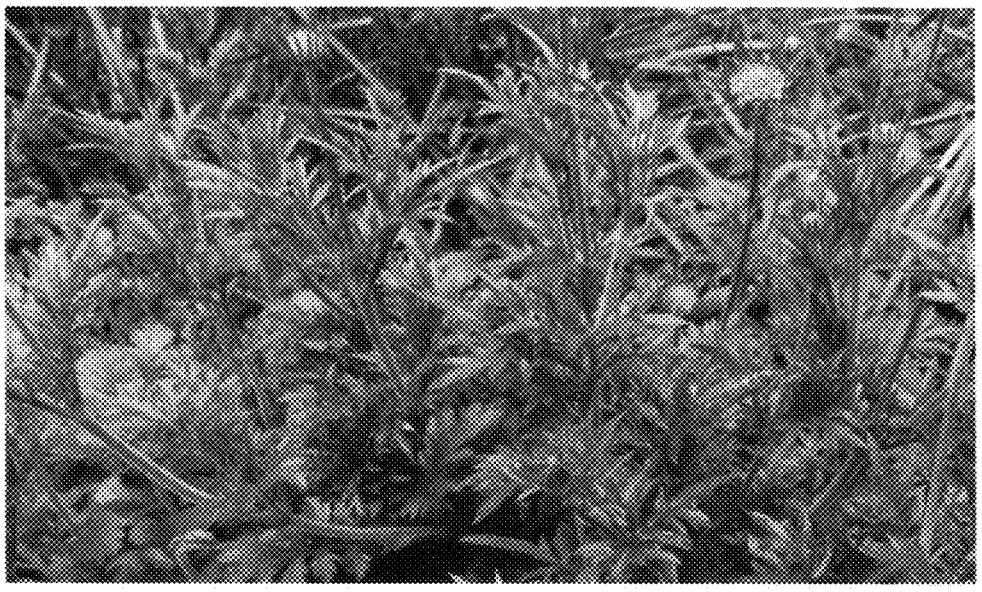

The photograph in FIG. 3 provides a side view of 'ICHPIN' 24 months in age as grown in a private garden in Maldon, Essex, United Kingdom.

The colors in the photographs may differ slightly from the color values cited in the detailed botanical description, which accurately describes the colors of the new *Scabiosa*.

DETAILED BOTANICAL DESCRIPTION

The following is a detailed description of 18 month-old plants from rooted cuttings of the new cultivar as grown in 5-liter containers in Maldon, Essex, United Kingdom. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—May through November in the United Kingdom and Netherlands and has shown continuous bloom 12 months and longer in Mediterranean climates of California.

*Plant habit*.—Herbaceous perennial herb, upright with extended flowering stems.

*Height and spread*.—Reaches an average of 90 cm in height (foliage height of 50 cm) and 55 cm in spread.

*Cold hardiness*.—Cold hardy at least to U.S.D.A Zone 7.

*Disease and pest resistance*.—No susceptibility or resistance to diseases or pests has been observed, plants have been observed to be healthy to date.

*Root description*.—Fine and fibrous.

*Propagation*.—Stem cuttings.

*Root development*.—Roots initiate in 10 to 14 days under greenhouse conditions and rooting cutting plugs will develop to a flowering plant in a 1.5-liter container in 4 months.

*Growth rate*.—Moderate.

Stem description:

*Stem shape*.—Cylindrical.

*Stem color*.—145B to 145C.

*Stem size*.—Up to 35 cm in length and 4 mm in width.

*Stem surface*.—Pubescent with un-branched hairs.

*Stem strength*.—Strong, held primarily upright.

*Branching habit*.—Freely branching with many spreading branches from the base.

Foliage description:

*Leaf division*.—Lower leaves; single, middle leaves; pinnatifid to pinnatisect in upper part of the leaf with 1 to 2 or more pairs of lobes in lower part of the leaf, upper leaves; pinnatisect.

*Leaf shape*.—Lower leaves; ovate, middle leaves; narrow obovate, upper leaves; ovate.

*Leaf base*.—Lower leaves; decurrent, middle leaves; decurrent, upper leaves; obtuse.

*Leaf apex*.—Lower leaves; obtuse, middle leaves; obtuse, upper leaves; acute.

*Leaf margin*.—Lower leaves; serrate, middle leaves; lobes and leaf divisions have teeth, upper leaves; deeply divided.

*Leaf venation*.—Pinnate, color on upper and lower surface N144D.

*Leaf attachment*.—Petiolate.

*Leaf arrangement*.—Opposite.

*Leaf surface*.—Pubescent, upper surface; short, straight translucent hairs, lower surface; recurved unbranched transluscent hairs.

*Leaf color*.—Upper surface; 143C, lower surface; 143D.

*Leaf size*.—Lower leaves; 5.5 cm in length (including petiole) and 1.5 cm in width, middle leaves; 5.5 cm in length (including petiole) and 1.5 cm in width, upper leaves; Up to 5.5 cm in length and 2.5 cm in width.

*Leaf number*.—Average of 14 per main branched stem.

*Leaf fragrance*.—None.

*Internode length*.—Up to 4 cm in length.

*Petiole*.—Up to 3.5 mm in length and 1.5 mm in width, 145B in color, surfaces are covered with un-branched translucent hairs.

Flower description:

*Inflorescence type*.—Flat topped heads of florets subtended by leafy, involucral bracts, solitary.

*Lastingness of inflorescence*.—Average of 10 days, self cleaning.

*Inflorescence size*.—An average of 1.7 cm in depth and 5.25 cm in diameter.

*Inflorescence fragrance*.—None.

*Inflorescence number*.—An average of 1 flowering head on each peduncle, outer florets 15 to 25, inner florets an average of 50.

*Floret form*.—Tubular.

*Floret aspect*.—Held outward to upward.

*Floret buds*.—Average of 3 mm in depth and diameter, N74B in color, obovate in shape.

*Floret size*.—Up to 1.5 cm in length and diameter.

*Corolla*.—Outer florets; 5 lobes, narrow in shape with 3 obovate shaped upper lobes and 3 round shaped lower lobes, base is fused to tube, all surfaces are smooth and covered with pubescence, margins are wavy, upper lip is an average of 1.5 cm in length and 1.5 cm in width, upper surface color is between N78C and N74C, lower surface color is N74D and blending to 155A near apex, lower lip is an average of 4 mm in length and 6 mm in width, upper surface color is between N78C and N74C, lower surface color is N74D and blending to 155A near apex, inner florets; 5 lobes, narrow in shape with 3 oblong shaped upper lobes and 2 round shaped lower lobes, base is fused to tube, all surfaces are smooth and covered with pubescence, margins are smooth, upper lip is an average of 4 mm in length and 5 mm in width, upper and lower surface color is N74D and blending to 155A near apex (particularly as temperatures cool), lower lip is an average of 1 mm in length and 3 mm in width, upper and lower surface color is N74D and blending to 155A near apex, tube; outer florets 5 to 7 mm in length and 1 to 2 mm in diameter, 155A in color, smooth on inner and outer surfaces, inner florets 4 to 5 mm in length and 1 to 2 mm in diameter, 155A in color, smooth on inner and outer surfaces.

*Involucels*.—Cup shaped, scarious with a triangular shaped top, outer florets an average of 1.5 mm in length and 2 mm in width and inner floret an average of 2 mm in length and 2 mm in width, persistent and enlarging with fruit (encloses ovary),155A with linear markings about 145D in color, surfaces are pubescent with a few long hairs.

*Sepals*.—Outer florets; 5, thread like and stiff in shape, an average of 8 mm length, <0.5 mm in width, entire margin, surface minutely hairy, acute apex, truncate base, N186B to N186C in color, inner florets; 5, thread like and stiff in shape, an average of 3 mm length, <0.5 mm in width, entire margin, surface is minutely hairy, acute apex, truncate base, N186B to N186C in color.

*Peduncles*.—An average of 20 to 30 cm in length and 2 mm in diameter, pubescent surface, 143C in color.

*Pedicels*.—Individual flowers sessile.

*Involucral bracts*.—An average of 15, arrangement is whorl around flower head, linear in shape, about 1 cm in depth and 1 mm in width, surfaces are pubescent, color; 143B with base 145D, apex acute, base truncate, margins entire, held nearly horizontally.

Reproductive organs:

*Gynoecium*.—Outer florets; pistil; 1, stigma; is capitate shaped, <1 mm in length and width and 75A in color, style; linear in shape, an average of <0.5 mm in length, 75B, in color and shading to 155A in color at base, ovary; cylindrical in shape, inferior, <1 mm in height and 1.5 mm in width, surface is minutely pubescent and 146D in color, inner florets; pistil; 1, stigma; is capitate in shape, <1 mm in length and width and 75A in color, style; linear in shape, an average of 1.5 mm in length and 0.5 mm in width, 75B and shading to 155A in color at base, ovary; cylindrical in shape, inferior, <1 mm in height and <1 mm in width, surface is minutely pubescent and 145D in color.

*Androcoecium*.—Outer florets; stamens; 4, just exceeding corolla tube, attached to corolla lobes, anthers; NN155D in color, 1 mm in length and <0.5 mm in width, filaments; an average of <1 mm in length and <0.5 mm in width, and NN155D in color, pollen not observed, inner florets; stamens; 4, just exceeding corolla tube, attached to corolla lobes, anthers; NN155D in color, <1 mm in length and <0.5 mm in width, filament; is an average of <1 mm in length and <0.5 mm in width, and 155A in color, pollen not observed.

*Fruit/seeds*.—Seed is produced; average of 1 achene per each flower, cylindrical in shape, individual seed size is 3 mm in length and 1 mm in width and 195B in color.

It is claimed:

1. A new and distinct cultivar of *Scabiosa* plant named 'ICHPIN' as herein illustrated and described.

* * * * *